United States Patent [19]

Bonjouklian et al.

[11] Patent Number: 4,659,859
[45] Date of Patent: Apr. 21, 1987

[54] 2-ALKOXY-1-ALKOXY PHOSPHORYL DICHLORIDES

[75] Inventors: Rosanne Bonjouklian; Michael L. Phillips, both of Indianapolis, Ind.

[73] Assignee: Eli Lilly and Company, Indianapolis, Ind.

[21] Appl. No.: 888,905

[22] Filed: Jul. 24, 1986

Related U.S. Application Data

[62] Division of Ser. No. 627,322, Jul. 2, 1984, abandoned.

[51] Int. Cl.$^4$ ................................................ C07F 9/14
[52] U.S. Cl. ..................................... 558/188; 558/169
[58] Field of Search ........................................... 558/188

[56] References Cited

U.S. PATENT DOCUMENTS 4,426,330  1/1984  Sears .................................... 260/403
4,426,529  1/1984  Hosumi et al. ........................ 546/22

FOREIGN PATENT DOCUMENTS 92190  10/1983  European Pat. Off.

Primary Examiner—Anton H. Sutto
Attorney, Agent, or Firm—Bruce J. Barclay; Leroy Whitaker

[57] ABSTRACT

2-Alkoxy $C_{12-26}$ straight-chain alkyl hydroxyphosphoryl cholines, useful as hypotensive agents, anti-cancer agents and as anti-inflammatory agents.

1 Claim, No Drawings

2-ALKOXY-1-ALKOXY PHOSPHORYL DICHLORIDES

This application is a division of application Ser. No. 627,322, filed July 2, 1984, now abandoned.

BACKGROUND OF THE INVENTION

The term "phospholipid" is generic to several different types of compounds originating in the mammalian cell and containing long chain fatty acid esters of glycerol attached to various polar groupings. Lecithin, a phosphatidic acid ester of choline, is one of a group of phospholipids of structure I below

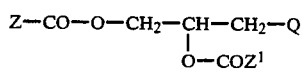

wherein Z and $Z^1$ are long straight chain alkyl or alkenyl radicals and Q is

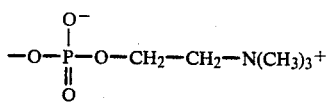

A related substance is platelet-activating factor (PAF)—see Demopoulos et al, *J. Biol. Chem.*, 254, 9355 (1979)—having structure Ia below

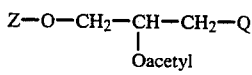

in which there is an ether linkage on C-1, a short chain fatty acid ester (acetate) at C-2, Z is $C_{16}$-$C_{18}$ alkyl and Q has its previous meaning. A number of analogues of PAF have been synthesized. Among these are compounds of structure Ib below described in *FEBS Letters*, 14 29 (1982)-see also Modell et al, *Can. Res.*, 39, 4681 (1979) which describe the activity of such compounds in selectively destroying Meth A sarcoma cells.

where $Z^2$ is alkyl or H; and Q has its previous meaning.

Other substitutions such as chloro for the C-2 acyloxy of PAF are known.

Diethers of structure Ic are also known—

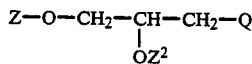

See U.S. Pat. No. 4,426,525 where Z is tridecyl or tetradecyl.

The compound wherein Z is $C_{18}H_{37}$ and $Z^2$ is methyl inhibits the proliferation of leukemic cells according to Tidwell et al., *Blood*, 57, 794 (1981)—See also Derwent Abstract 17735 K/08 and Derwent Abstract 98882 E/46.

Compounds lacking the C-1 oxygen have also been prepared; i.e., compounds of the structure

where Z is $C_{13}$-$H_{27}$(CAS 51814-79-0); Z is $C_{12}H_{25}$ and the C-2 hydroxyl is esterified (CAS 54646-41-2) and Q has its previous meaning—see also Derwent Abstract 12632 K/06 (an ortho ester) and *Chem. Biochem. Res. Comm;* 54, 648 (1973) particularly Scheme 1, page 652, and related disclosure.

Ethers of compounds according to Id have recently been disclosed in EPO application No. 92,190 published Oct. 26, 1983 based on G.B. No. 82-11284 filed Apr. 19, 1982, as represented by formula Ie

where Z is alkyl, alkoxy or alkanoylamino and $Z^1$ is lower alkyl, lower alkanesulfonyl or arenesulfonyl. dl-2-Methoxy-1-[(2-trimethylaminoethoxy)phosphinyloxy]-octadecane, hydroxy inner salt, is specifically disclosed. The compounds inhibit the growth of Meth A sarcoma transplanted in mice.

SUMMARY OF THE INVENTION

This invention provides 2-alkyloxy-1-[(2-tri($C_{1-2}$ alkyl)aminoethoxy)phosphinyloxy]$C_{12-26}$ alkanes, hydroxy inner salts, of the formula

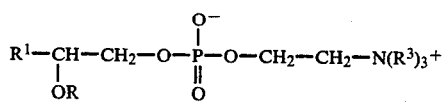

wherein R is $C_{1-6}$ alkyl preferably $C_{1-3}$ straight chain alkyl, $R^1$ is straight-chain $C_{10-24}$ alkyl and each $R^3$ is individually methyl or ethyl. R in the above formula includes methyl, ethyl, n-propyl, isobutyl, n-amyl, isoamyl, n-hexyl, sec-butyl, isopropyl and the like, and $R^1$ includes decyl, undecyl, dodecyl, tridecyl, tetradecyl, pentadecyl, hexadecyl, octadecyl, eicosanyl, trieicosanyl, tetraeicosanyl and the like groups.

A preferred group of compounds of this invention are those according to II in which $R^1$ is straightchain $C_{12-18}$. Another preferred group is constituted of those compounds in which R is methyl or ethyl or in which $R^3$ is methyl.

The first major step in the synthesis of compounds according to II above is the provision of a key intermediate diol of the structure

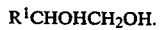

These diols have a center of asymmetry at C-2 and thus occur as racemic mixtures [a (d,l) or (±) pair]. These racemic alcohols can be resolved by methods available in the art such as by protecting the primary alcohol group by formation of a trityl ether thereon and then reacting the unprotected secondary alcohol group with an optically-active acid to form two diastereomeric esters. These diastereomers are not mirror images and thus can be separated mechanically; i.e., by fractional crystallization or chromatography.

Compounds according to III where $R^1$ is $C_{10-24}$ straight chain alkyl can be prepared by the following synthetic procedure based on *Org. Reactions*, 7, 378 (1957).

Reaction Scheme 1

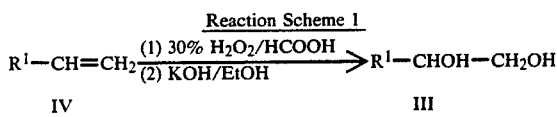

In this procedure, a terminally mono-unsaturated alkene (IV) is epoxidized with hydrogen peroxide in formic acid or with an organic peroxide such as a perbenzoic acid, i.e., m-chloroperbenzoic acid in $CHCl_3$. Further treatment of the epoxidation mixture with base yields the 1,2-diol (III).

Alternatively, the 1,2-diol can be prepared via a Wittig reaction in which glyceraldehyde ketal or acetal is reacted with a phosphorous ylide in the presence of a base such as butyl lithium to yield eventually, a $\Delta^3$-1,2-diol (IX), which can readily be hydrogenated to yield the desired intermediate, III. This procedure is illustrated below.

the synthetic procedure does not affect the asymmetric center.

Alternatively, if Reaction Scheme II uses as a starting material an optically active glyceraldehyde ketal; i.e., D-(+)-glyceraldehyde ketal, the D-(+)-diol final product can be transformed to the corresponding isomeric L-(−) diol by Walden inversion using an intermediate diester of a strong organic acid such as p-toluenesulfonic acid or methanesulfonic acid. The procedure used follows that of Hirth et al., *Helv. Chim. Acta*, 66, 1210 (1983). The dimesylester of a D-(+) diol is prepared with mesyl chloride in pyridine. The diester is then heated with acetic anhydride and potassium acetate or other acetic acid salt to yield the diacetate of the L-(−) diol. Hydrolysis of the diacetate with base ($K_2CO_3$) yields the L-(−) diol.

Reaction Scheme III below illustrates this synthetic procedure.

Reaction Scheme II

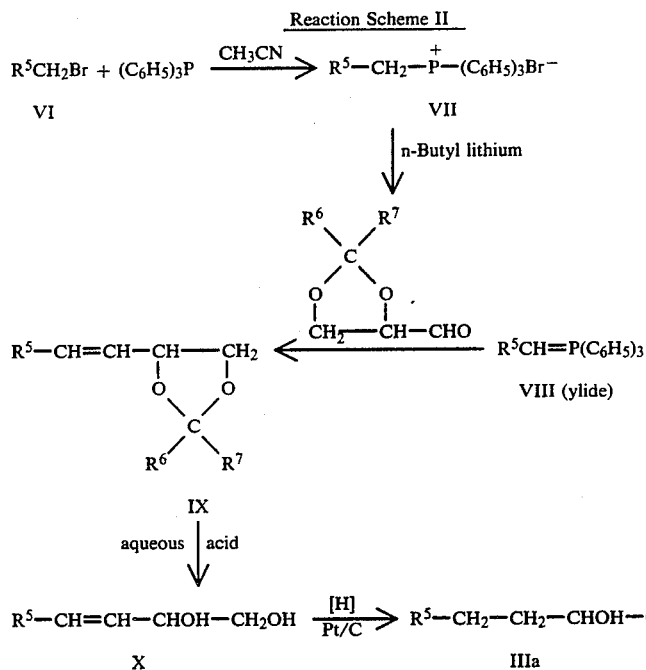

where $R^5$ is $C_{8-22}$ straight chain alkyl ($R^1=R^5-CH_2-CH_2$), and $R^6$ and $R^7$ are lower alkyl ($C_{1-3}$ alkyl) or $R^6$ is H and $R^7$ is benzyl.

In Reaction Scheme II, the first step involves reaction of the alkyl halike with triphenylphosphine in a suitable solvent such as actonitrile, followed by formation of the ylide, and finally, reaction of the ylide with the glyceraldehyde ketal or acetal. Removal of the ketal protecting group is carried out in aqueous acid; i.e., acetic, p-toluenesulfonic and the like. The final step, reduction of the double bond, involves the use of a noble metal catalyst-Pt, Pd, Rd-in an Adams machine with low hydrogen pressures; i.e., 15-60 psi.

Reaction Scheme II has an advantage not possessed by other reaction schemes in that an optically active glyceraldehyde ketal can be a reactant; a D-(+)-glyceraldehyde ketal or L-(−)-glyceraldehyde ketal; i.e., aldehydes derived by oxidation of D-mannitol-1,2,5,6-diacetonide or L-mannitol-1,2,5,6-diacetonide, respectively, with lead tetraacetate. Use of this optically-active aldehyde yields an optically-active diol since

Reaction Scheme III

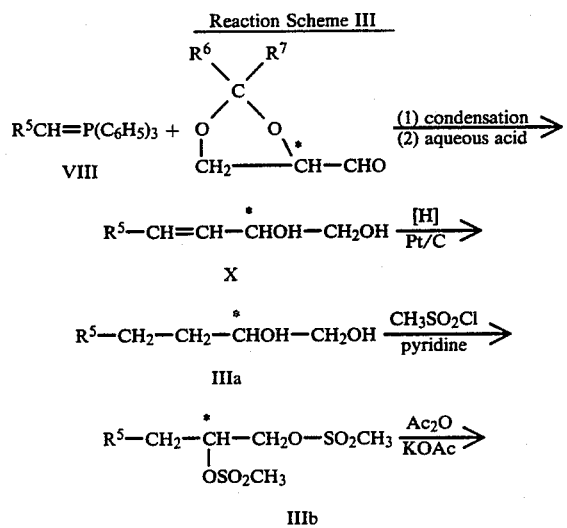

-continued
Reaction Scheme III

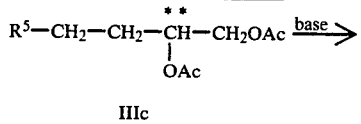

IIIc

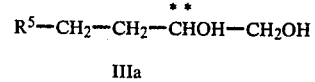

IIIa where C* indicates an optically active carbon, C** indicates an optically-active carbon of opposite configuration, and $R^5$, $R^6$, and $R^7$ have their previous meaning.

Once the key intermediate diol, III ($R^1$-CHOH-CH$_2$OH), has been prepared (which diol can be either racemic or optically active), it can be converted to a compound represented by II above according to the following procedure:

Reaction Scheme IV

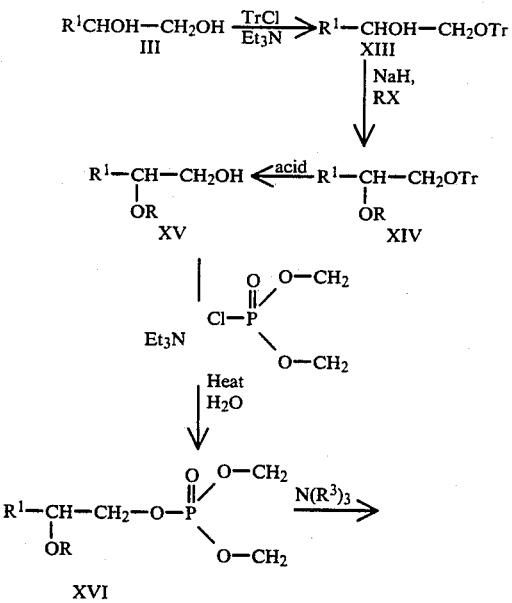

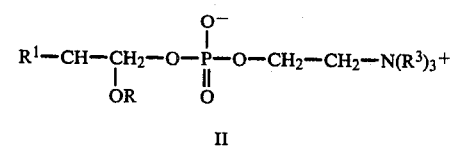

II wherein R, Rhu 1 and $R^3$ have their previous meaning and Tr is trityl [(C$_6$H$_5$)$_3$C]. In the above reacting scheme, the primary alcohol group of III is reacted with a protecting group such as the trityl (triphenylmethyl) group by reaction with, for example, trityl chloride to form a trityl ether on the primary hydroxyl. Other protecting groups which are base stable but acid unstable and which can be used as part of a reagent to etherify a primary alcohol group preferentially include the t-butyldimethylsilyl, diphenylmethylsilyl and the like. The reaction which preferentially etherifies the primary hydroxyl should be run under mild reaction conditions to avoid a competing reaction with the secondary hydroxyl.

With the primary hydroxyl protected, the secondary hydroxyl can be etherified under non-acidic conditions (base, non-aqueous solvent) with a compound of the formula RX wherein R has its previous meaning and X is an acid unstable leaving group (group susceptible to anionic displacement) such as halogen, p-tosyl, mesyl and the like. Useful compounds of structure RX include alkyl halides such as alkyl iodides, bromides or chlorides. The ultimate product is an ether $$R^1-\underset{\underset{OR}{|}}{CH}-CH_2OTr. \qquad (XIV)$$

Sodium hydride in tetrahydrofuran (THF) is conveniently employed to form the salt of the secondary alcohol group.

The primary alcohol is next de-protected under acidic conditions; i.e., the trityl group is removed, as for example with p-toluenesulfonic acid in an inert mutual solvent such as CH$_2$Cl$_2$/MeOH, to yield a primary alcohol of the formula $R^1$-CHOR-CH$_2$OH. The alkyl ether at C-2 is of course, stable to acid.

An alternate route to XV, the 2-alkoxy 1-hydroxyalkane, involves the epoxidation of the starting material from Reaction Scheme I, the terminally unsaturated derivative, $R^1$—CH=CH$_2$ (IV), with, for example, m-chloroperbenzoic acid in methylene dichloride to form an epoxide (XVII). This reaction is followed by an opening of the epoxide ring with a lower alkanol (ROH) in the presence of a Lewis acid such as borontrifluoride etherate in a mutual inert solvent. A mixture of ethers: ie, a 2-alkoxy-1-alkanol and a 1-alkoxy-2-alkanol, is obtained. Preparative chromatography easily separates the two ether-alcohols to yield XV, the desired 2-alkoxy-1-alkanol, in 34% overall yield. The above procedure is based on that of *JACS*, 68, 680 (1946). Reaction Scheme V below illustrates the above procedure.

Reaction Scheme V

R'—CHOR—CH$_2$OH + R'—CHOH—CH$_2$OR
XV                                   XVa

The primary alcohol (XV) is next reacted with 2-chloro-1,3,2-dioxaphospholane-2-oxide

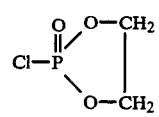

in a neutral non-reacting solvent (ether, THF, THP) in the presence of an organic base (triethylamine, pyridine, quinoline) at room temperature or below under a N$_2$ atmosphere, following the procedure of *Bull. Soc. Chim.*, 667, (1974). The product of this reaction is the cyclic phosphate (XVI). Reaction of this cyclic phosphate with a trialkylamine N(R$^3$)$_3$ at elevated temperature (about 60° C.) in a non-reacting solvent, under pressure if necessary, yields a compound according to structure II. In the reaction with the trialkylamine, a useful solvent is acetonitrile.

An alternative scheme for preparing the compounds of this invention starting with the intermediate XV (from Reaction Scheme IV or Reaction Scheme V) is set forth in Reaction Scheme VI below, following the procedure of *Lipids,* 14, 88 (1978).

Reaction Scheme VI

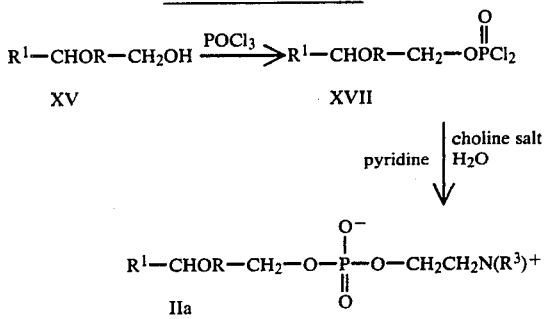

wherein R, $R^3$ and $R^1$ have their previous meanings.

Since choline is a trimethylammonium compound, the above scheme illustrates the preparation of compounds in which all $R^3$'s are methyl. If it is desired to prepare compounds in which at least one $R^3$ is other than methyl, intermediates of the structure

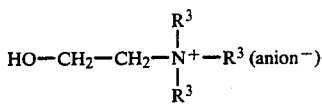

are used wherein each $R^3$ is methyl or ethyl, but one $R^3$ is other than methyl.

This invention is further illustrated by the following specific examples.

EXAMPLE 1

Preparation of (d,l)-2-Methoxy-1-[(2-trimethylaminoethoxy)phosphinyloxy]eicosane, hydroxy inner salt A reaction mixture was prepared from 111.8 g of 1-eicosene, 470 ml of 98–100% formic acid and 47.5 ml of 30% $H_2O_2$. The reaction mixture was maintained at about 40° C. 23.8 additional mls of 30% $H_2O_2$ were added at 18 and 27 hours and 47.5 additional mls at 40 and 68 hours. After 93 hours, the reaction was terminated and the reaction mixture evaporated to dryness. The residue, comprising a mixture of formate esters formed in the above reaction, was treated with 399 ml of 3N ethanolic potassium hydroxide at reflux temperatures for about 1 hour, thus forming (dl)-1,2-dihydroxyeicosane. The reaction mixture was cooled and the volatile constituents removed by evaporation in vacuo. Recrystallization from chloroform yielded one-spot material on silica gel; Rf =0.4 (1:1 cyclohexane/ethyl acetate); weight=77.5 g (61.8%).

A reaction mixture, prepared by mixing 77.1 g of the above diol, 735 ml of hexane, 37.6 ml of triethylamine and 68.3 g of trityl chloride, was heated to reflux for about 3 days. It was then cooled, and the hexane removed by evaporation. Equal volumes of chloroform and water were added. The chloroform layer was separated. The aqueous layer was extracted with an equal volume of chloroform, and the two chloroform extracts combined. The combined extracts were dried and the chloroform removed by evaporation. The residue, comprising (d,l)-1-trityloxy-2-hydroxyeicosane formed in the above reaction, was dissolved in n-hexane (60°-68° C.) and the solution cooled. The resulting crystals were separated by filtration and the filtrate evaporated to dryness. Crystallization of the resulting residue from diethylether yielded 71.8 g (73%) of (d,l)-1-trityloxy-2-hydroxyeicosane; Rf=0.3 (5:1 cyclohexane/ether).

A solution, prepared by dissolving 586.2 mg of (d,l)-1-trityloxy-2-hydroxyeicosane in 4.2 ml of THF (tetrahydrofuran), was poured into a carefully dried flask equipped with condenser under a positive $N_2$ flow 37.9 mg of sodium hydride were added and the reaction mixture heated to about 65° C. for 2 hours. The reaction mixture was cooled to room temperature and 0.328 ml of methyl iodide (747 mg) were added by syringe. This new reaction mixture was heated to about 65° C. overnight and was then cooled to room temperature. Five drops of water were added followed by 5 ml. of chloroform. The chloroform layer was separated, washed once with water and then dried. Evaporation of the solvent left a residue which was redissolved in chloroform and again evaporated to dryness to remove traces of THF. The resulting residue, comprising (d,l)-1-trityloxy-2-methoxyeicosane, weighed 616.7 mg. NMR ($CDCl_3$) showed a peak at 3.4 $\delta$, but no peak attributable to the hydroxyl hydrogen; $R_f$=0.8 (5:1 cyclohexane/ether).

A solution of 570.9 mg of crude (d,l)-1-trityloxy-2-methoxyeicosane in 4 ml of glacial acetic acid was placed in a dried 3-necked equipped with stirrer under a nitrogen atmosphere. The flask was cooled to about 15° C. Gaseous HBr was passed into the solution. When the reaction (removal of the trityl protecting group) was shown to be complete by TLC., the reaction mixture was poured into an ice-water mixture. An equal volume of chloroform was added, followed by sufficient saturated aqueous sodium bicarbonate to bring the pH of the aqueous layer to about 5.5. The $CHCl_3$ layer was separated and washed successively with saturated aqueous sodium bicarbonate and water. The chloroform layer was dried and the chloroform removed by evaporation. A chloroform solution of the residue was chromatographed over 20 g of silica gel. Cyclohexane containing increasing amounts of ether (0–18%) was used as the eluant. Fractions containing (d,l)-1-hydroxy-2-methoxyeicosane formed in the above reaction were combined. $R_f$=0.2 (3:1 cyclohexane ether).

A reaction mixture prepared by mixing 657.3 mg of (d,l)-1-hydroxy-2-methoxyeicosane, 10 ml of THF and 0.293 ml of triethylamine was cooled with stirring to about 0° C. in an ice bath. 0.19 ml of 2-chloro-1,3,2-dioxaphospholane-2-oxide were added gradually by syringe over a 30 minute period. After 15 minutes, the ice bath was removed and the reaction mixture allowed to warm to room temperature where it was stirred overnight. TLC (1:1 cyclohexane/EtOAc) indicated the reaction was complete. The reaction mixture was filtered, and the filtrate evaporated to dryness in vacuo. The residue was twice triturated with $CH_2Cl_2$. 973.3 mg of crude (d,l)-2-[(2-methoxyeicosyl)oxy]-1,3,2-dioxophospholane-2-oxide were thus obtained.

973.3 mg of the above crude cyclic phosphate ester were added to 0.546 ml of trimethylamine in a pressure tube cooled to $-80°$ C. followed by the addition of 6 ml of acetonitrile. The tube was sealed and then heated in a 60° C. bath overnight. A precipitate, comprising (dl)-2-methoxy-1-[(2-trimethylaminoethoxy)phosphinyloxy]eicosane, hydroxy inner salt, formed in the above reaction, was collected by filtration. The precipitate was washed with $CHCl_3$. Evaporation of the filtrate yielded more of the desired product. Chromatography over 25 g of neutral alumina using chloroform containing increasing amounts of methanol (0-33%) yielded 403.2 mg of (d,l)-2-methoxy-1-[(2-trimethylaminoethoxy)phosphinyloxy]eicosane, hydroxy inner salt, melting at about 230° C.; $R_f=0.2$ (10:5:1 chloroform/methanol/NH$_4$OH).

EXAMPLE 2

Preparation of (d,l)-2-Ethoxy-1-[(2-trimethylaminoethoxy)phosphinyloxy]eicosane, hydroxy inner salt Following the above procedure, 8.2 g of NaH (60% in oil) were placed in a flask under a N$_2$ atmosphere. The oil was removed with hexane to leave 4.92 g NaH in the flask. 166 ml of THF were added followed by 46.2 g of (d,l)-1-trityloxy-2-hydroxyeicosane (prepared by the method of Example 1). The reaction mixture was heated to reflux for about 2 hours to form the sodium salt of the secondary alcohol group. 24 ml of ethyl iodide were added and the reaction mixture heated to reflux temperature for about 2 hours. The reaction mixture was worked up as in Example 1 except that the combined chloroform extracts were washed with an equal volume of saturated aqueous sodium chloride (brine) prior to drying and removing the solvent by evaporation. 47.9 g of crude 1-trityloxy-2-ethoxyeicosane were obtained. The product, without further purification, was placed in a flask with 415 ml of CH$_2$Cl$_2$, 415 ml of methanol and 1.58 g of p-toluene sulfonic acid monohydrate. The mixture was stirred overnight at room temperature; then 500 ml of 1N aqueous sodium hydroxide and 390 ml of CH$_2$Cl$_2$ were added. The organic layer was separated, and the aqueous layer extracted with an additional 390 ml of CH$_2$Cl$_2$. The combined extracts were washed with 390 ml of brine and then dried. Evaporation of the solvent yielded 47.26 g of (d,l)-1-hydroxy-2-ethoxyeicosane. The product was further purified by preparative HPLC over silica using a cyclohexane/ether eluant; yield=15.9 g (52.2%).

Following the above procedure, 1.03 g of the ethyl ether, [($R_f=0.02$ (3:1 cyclohexane/ether)] was reacted with 2-chloro-1,3,2-dioxaphospholane-2-oxide to yield 1.53 g of crude (d,l)-2-[(2-ethoxyeicosyl)oxy]-1,3,2-phospholane-2-oxide.

Following the procedure of Example 1, the above crude phosphate ester was reacted with trimethylamine in acetonitrile solution in a sealed tube. A crude yield of 76.9% (1.1714 g) of the quaternary amine zwitterion was obtained. Chromatography as in Example 1 gave 1.04 g (68.3% yield) of purified (d,l)-2-ethoxy-1-[(2-trimethylaminoethoxy)phosphinyloxy]eicosane, hydroxy inner salt melting at about 237° C. with early softening; $R_f=0.2$ (10:5:1 CHCl$_3$/MeOH/NH$_4$OH).

EXAMPLE 3

Alternate Procedure for Preparing (d,l)-2-Ethoxy-1-[(2-trimethylaminoethoxy)phosphinyloxy]eicosane, hydroxy inner salt (d,l)-1-Hydroxy-2-ethoxyeicosane, produced by deprotecting the corresponding 1-trityloxy derivative of Example 2, was reacted with POCl$_3$ in THF solution in the presence of triethylamine; (13.1506 g of eicosane, 200 ml THF, 10.7 ml Et$_3$N and 5.37 ml POCl$_3$) to yield (d,l)-2-ethoxy-1-eicosyloxyphosphoryl dichloride. Using a water-free apparatus and under an N$_2$ atmosphere, a solution of (d,l)-2-ethoxy-1-hydroxyeicosane and Et$_3$N in THF was added in dropwise fashion to the POCl$_3$ in THF solution over a 15 minute period. This reaction mixture was stirred for about 1 hour at room temperature, at which time TLC showed that the reaction was substantially complete (no spot corresponding to starting material). The solution was filtered to remove triethylamine hydrochloride formed as a by-product in the reaction. This precipitate was washed twice with THF. The filtrate was concentrated in vacuo. The resulting residue was triturated once with toluene and the toluene removed in vacuo. The residue, comprising (d,l)-2-ethoxy-1-eicosyloxyphosphoryl dichloride, was then used as the starting material in the next step of the reaction.

The above product was dissolved in a mixture of 230 ml of purified CHCl$_3$ and 24.3 ml of pyridine in an N$_2$ atmosphere commerical. (Commerical CHCl$_3$ was passed over alumina prior to use to remove the ethanol present as a stabilizer.

Choline tosylate (23.26 g) was added and the resulting solution stirred at room temperature for 5 hours. 5.7 ml of H$_2$O were then added and the new mixture stirred for one-half hour.

Next, 360 ml of CHCl$_3$ and 120 ml of H$_2$O were added with thorough mixing, followed by 120 ml of methanol to break the resulting emulsion. The organic layer was separated and then washed with 120 ml of saturated aqueous sodium bicarbonate. 120 ml of additional methanol were added. The organic layer was dried and the solvent removed therefrom in vacuo. The resulting residue was chromatographed over 200 g of silica gel 60. CHCl$_3$ with increasing amounts (0-80%) MeOH was used as the eluant. Fractions containing (d,l)-2-ethoxy-1-[(2-trimethylaminoethoxy)phosphinyloxy]eicosane, hydroxy inner salt, were combined, and the product isolated by evaporation of the eluting solvent; yield=8.4 g.

EXAMPLE 4

Preparation of (d,l)-2-Ethoxy-1-[(2-trimethylaminoethoxy)phosphinyloxy]hexadecane, hydroxy inner salt Following the procedure of Example 2, (d,l)-1,2-dihydroxyhexadecane was tritylated to produce (d,l)-1-trityloxy-2-hydroxyhexadecane. Reaction of this protected primary alcohol product with sodium hydride followed by reaction of the sodium salt with ethyl iodide in THF gave (d,l)-1-trityloxy-2-ethoxyhexadecane which was purified by the procedure of Example 2. The tritylated product was deprotected by treatment with p-toluenesulfonic acid in 1:1 CH$_2$Cl$_2$/MeOH to yield (d,l)-2-ethoxyhexadecanol in about 55-60% overall yield. About 18.5 g of this product were reacted with POCl$_3$ in THF in the presence of Et$_3$N by the method of Exam- 3 to yield (d,l)-2-ethoxy-1-hexadecanyloxyphosphoryl dichloride. The dichloride was reacted with choline tosylate by the procedure of Example 3 to give (d,l)-2-ethoxy-1-[(2-trimethylaminoethoxy)phosphinyloxy]hexadecane, hydroxy inner salt; yield (crude)=35.13 g. Chromatography as in Example 3 gave about 10 g of purified compound; $R_f=0.2$ (10:5:1 CHCl$_3$/MeOH/NH$_4$OH).

EXAMPLE 5

Preparation of (d,1)-2-Ethoxy-1-[(2-trimethylaminoethoxy)phosphinyloxy]dodecane, hydroxy inner salt (d,1)-1-Trityloxy-2-hydroxydodecane, furnished by the procedure of Example 1, was reacted successively with NaH and EtI in THF to yield (d,1)-1-trityloxy-2-ethoxydodecane. The product was isolated by the procedure of that Example and the crude diether deprotected with p-toluene sulfonic acid by the procedure of Example 2 to yield (d,1)-2-ethoxy-1-dodecanol in 45% overall yield. This primary alcohol can be reacted with $POCl_3$ to yield (d,1)-2-ethoxy-1-dodecanyloxyphosphoryl dichloride, reaction of which with choline tosylate gives (d,1)-2-ethoxy-1-[(2-trimethylaminoethoxy)phosphinyloxy)dodecane, hydroxy inner salt. $R_f$=0.2 (10:5:1 $CHCl_3$/MeOH/$NH_4OH$).

EXAMPLE 6

Preparation of D-2-Ethoxy-1-[(2-trimethylaminoethoxy)phosphinyloxy]eicosane, hydroxy inner salt In a Wittig reaction, 25 g of 1-bromoheptadecane was reacted with 20.53 g of triphenylphosphine in 15.7 ml of acetonitrile. The reaction mixture was heated to about 80° C. overnight. The volatile constituents were removed by evaporation to yield a white gelatinous mass. This residue was triturated with 175 ml of toluene and 300 ml of diethyl ether. After stirring overnight, the mixture was filtered. The precipitate, comprising heptadecyltriphenylphosphonium bromide, weighed 37.2 g after drying $R_f$=0.3 (1:1 chloroform/acetone). 27.63 g of this phosphonium salt in 100 ml of THF were treated with 31.25 ml of 1.6M n-butyl lithium (in hexane) at 5° C. over a 5–10 minute period to form the ylide $(C_6H_5)_3P=CH-C_{16}H_{33}$ in situ. The reaction mixture was stirred for 5 minutes at 10° C., at which time 50 ml of DMSO were added followed by 6.5087 g of D-glyceraldehyde acetonide. This new reaction mixture was kept below 30° C. with stirring for 30 minutes. It was then quenched by the careful addition of 800 ml of water. The aqueous mixture was extracted with three 800 ml portions of petroleum ether. The combined organic extracts were dried. Evaporation of the solvent yielded a residue which was purified by chromatography. 15.1771 (86.1% yield) of D-1,2-dihydroxy-3-eicosene acetonide were obtained; $R_f$=0.6 (10:1 cyclohexane/ether). The acetonide protecting group was removed by heating the compound in a 2:1 acetic acid-water mixture overnight at 60°–65° C. The product, D-1,2-dihydroxy-3-eicosene weighing 13.45 g; $R_f$=0.5 (1:1 cyclohexane/ethyl acetate), was dissolved in about 2000 ml of ethyl acetate and hydrogenated at 15 psi using 4.3 g of 5% Pt-on-C catalyst. The catalyst was separated by filtration and the filtered catalyst washed thoroughly with ethyl acetate and chloroform. The filtrate and washings were combined, and the solvents evaporated therefrom in vacuo to leave a residue comprising D-1,2-dihydroxyeicosane. Recrystallization from n-hexane (B.P.=60°–68° C.) gave 10.09 g (74.5%) yield of purified compound. The compound was tritylated by the process of Example 1 to yield D-1-trityloxy-2-hydroxyeicosane (64.3% yield of purified compound). This tritylated derivative was reacted by the method of Example 2 with sodium hydride to form an intermediate salt on the secondary alcohol followed by treatment with ethyl iodide, all in THF solution, to yield crude D-1-trityloxy-2-ethoxyeicosane. Still following the procedure of Example 2, the trityl group was removed by treatment with a catalytic quantity of p-toluenesulfonic acid in a 1:1 $CH_2Cl_2$/MeOH solvent to yield D-1-hydroxy-2-ethoxyeicosane. The compound was isolated and purified by the method of Example 2; yield=58.6% (1.7967 g from 4.98 g of 1-trityloxy-2-ethoxylicosane).

Next, following the procedure of Example 3, 1.7775 g of D-1-hydroxy-2-ethoxyeicosane were reacted with $POCl_3$ in the presence of triethylamine to yield D-2-ethoxy-1-eicosyloxyphosphoryl dichloride. The dichloride was then reacted with choline tosylate to yield D-2-ethoxy-1-[(2-trimethylaminoethoxy)phosphinyloxy]eicosane, hydroxy inner salt; yield=1.3008 g.

EXAMPLE 7

Preparation of L-2-Ethoxy-1-[(2-trimethylaminoethoxy)phosphinyloxy]eicosane, hydroxy inner salt A suspension of 9.2957 g of D-1,2-dihydroxyeicosane from Example 6 in 177 ml of $CH_2Cl_2$ was chilled to about 0° C. in a dried reaction vessel under a nitrogen atmosphere. 11.9 ml of pyridine were added followed by the addition of 5.72 ml of methanesulfonyl chloride. After the addition had been completed, the reaction mixture was allowed to warm to room temperature at which temperature it was stirred for 48 hours. Additional pyridine (2.4 ml) and methanesulfonyl chloride (1.14 ml) were added and stirring continued for about an additional 60 hours. 100 ml of an ice/water mixture were then added. A three-fold extraction with equal volumes of $CH_2Cl_2$ was next carried out. The combined organic phases were extracted twice with 100 ml portions of 1.0N aqueous hydrochloric acid, twice with 100 ml portions of 5% aqueous sodium bicarbonate followed by extraction with 100 ml of brine. The organic layer was dried, and the solvent removed therefrom in vacuo to yield 13.9 g of D-1,2-dimesyloxyeicosane formed in the above reaction. $R_f$=0.7 (1:1 cyclohexane/ethyl acetate).

906.1 mg of the above dimesylate were placed in a suitable reaction vessel to which were added 9.6 ml of acetic anhydride and 944.5 mg of potassium acetate. This reaction mixture was heated at 140° C. (reflux) for 1.5 hours. The volatile constituents were then removed in vacuo. 8 ml of $CH_2Cl_2$ were added. The $CH_2Cl_2$ was decanted and another 8 ml of $CH_2Cl_2$ added. This mixture was filtered and the filtrate washed with $CH_2Cl_2$. The combined organic extracts and washes were themselves washed twice with brine, twice with 5% aqueous sodium bicarbonate and again with brine, and were then dried. Evaporation of the solvent yielded a brown oil which was purified by flash chromatography over 33 g of silica gel using cyclohexane containing increasing amounts of ether (1–10%) as the eluant. 593.6 mg of L-1,2-diacetoxyeicosane (77.5% yield)—$R_f$=0.2 (5:1 cyclohexane/ether)—were obtained in the above reaction (which involved a Walden inversion at C-2 during replacement of the mesyl groups by acetyl groups).

Next, the acetate groups were hydrolysed in methanolic potassium carbonate. To 9.0017 g of L-1,2-diacetoxyeicosane in 56.4 ml of $CH_2Cl_2$ were added 6.8650 g of potassium carbonate in 117.9 ml of methanol. The hydrolysis mixture was stirred at room temperature for ½ hour. The volatile constituents were removed in vacuo. Some CHCl$_3$ was added, and the resulting mixture heated on the steam bath. Filtration thru celite, followed by a thorough washing of the celite filter cake with hot CHCl$_3$ and hexane, yielded a filtrate from which 3.9 g of L-1,2-dihydroxyeicosane were obtained. An additional 1.8 g were obtained from filtrates, washes and reextraction of the K$_2$CO$_3$ filter cakes.

L-1,2-dihydroxyeicosane thus obtained was converted to the benzylidene acetal by standard procedures. The acetal was analyzed for optical purity with a chiral shift reagent, tris[3-(heptafluoropropylhydroxymethylene)-d-camphoratoeuropium III according to the procedure of Myers, *Tetrahedron Letters*, 43, 3551(1983). The optical purity was shown to be greater than 80% enantiomeric excess.

The L-diol was subjected to the same series of reactions as for the (d,1)-diol in Example 1: tritylation with triphenylmethyl chloride and triethylamine in hexane solution gave L-1-trityloxy-2-hydroxyeicosane. (5.5685 g of L-diol gave 8.230 g of L-1-trityloxy-2-hydroxyeicosane; yield=83.9%). L-1-trityloxy-2-hydroxyeicosane was then converted to the 2-ethoxy derivative by the method of Example 2, first making the sodium salt and then treating the salt with ethyl iodide, both steps in THF. The yield was essentially quantitative. The compound was deprotected with p-toluene sulfonic acid in CH$_2$Cl$_2$/MeOH by the method of Example 1 to yield L-1-hydroxy-2-ethoxyeicosane; overall yield for two steps=82.5%.

Finally, following the procedure of Example 3, L-(2-ethoxy-1-eicosyloxy)phosphoryl dichloride was prepared from L-1-hydroxy-2-ethoxyeicosane and POCl$_3$. The phosphoryl dichloride was used as isolated without further purification to react with choline tosylate to form L-2-ethoxy-1-[(2-trimethylaminoethoxy)phosphinyloxy]eicosane, hydroxy inner salt, in a 36.1% over all yield.

EXAMPLE 8

Alternate Preparation of (d,1)-2-Methoxy-1-eicosanol

A solution of 18.98 g of m-chloroperbenzoic acid (85%) and 24.69 g of 1-eicosene in 440 ml of benzene was stirred overnight at ambient temperature under a N$_2$ atmosphere. At 16 hours, reaction was nearly complete by TLC (3:1 isooctane/ether, SiO$_2$) At 24 hours, the reaction mixture was filtered and the filter cake washed with benzene. The filtrate was washed with saturated aqueous NaHCO$_3$, and with brine and with then dried. The benzene was removed in vacuo and the residue triturated with chloroform; yield=26.1 g of (d,1)-1,2-epoxyeicosane formed in the above reaction; R$_f$=0.8 (2:1 cyclohexane/ether). The crude epoxide (7.41 g) was suspended in 75 ml of absolute methanol under anhydrous conditions and the suspension heated at about 50° C. with stirring until all of the epoxide had either dissolved or melted. Boron trifluoride etherate (0.123 ml) was added by syringe beneath the surface of the solvent while stirring and heating were continued. TLC indicated that the reaction, opening of the epoxide ring, had gone substantially to completion within five minutes. At 20 minutes, the reaction flask was removed from the heating bath and 345.5 mg of solid potassium carbonate added. The consequent mixture was stirred at ambient temperature for about five minutes and was then diluted with 150 ml of CH$_2$Cl$_2$ and 150 ml of H$_2$O. The methylene dichloride layer was separated, and the aqueous layer mixed with an equal volume of brine and the combined layers extracted with CH$_2$Cl$_2$. The CH$_2$Cl$_2$ layers were combined and the combined layers dried. Evaporation of the solvent in vacuo yielded a residue weighing 10.2 g comprising a 1:1 mixture of the isomeric methyl ethers: (d,1)-1-methoxy-2-eicosanol and (d,1)-2-methoxy-1-eicosanol. Preparative HPLC of the residue yielded 3.4383 g of (d,1)-1-methoxy-2-eicosanol, R$_f$=0.3 (3:1 cyclohexane/ether), and 2.7927 g of (d,1)-2-methoxy-1-eicosanol, R$_f$=0.2 (3:1 cyclohexane/ether).

The compounds of this invention as represented by formula II are cytostatic in that they inhibit the growth of human leukemic cells (CCRF-CEM cell line). Table 1 below gives the results of such testing of several compounds. In the Table, column 1 gives the name of the compound and column 2 the IC$_{50}$ (concentration giving 50% growth inhibition) in mcg/ml. Three compounds not comprehended by formula II are included for comparison.

TABLE 1

| Cell-Growth Inhibition | |
|---|---|
| Name of compound | IC$_{50}$ mcg/ml. |
| 1. D-(+)-2-ethoxy-1-[(2-trimethylaminoethoxy)phosphinyloxy]eicosane, hydroxy inner salt | 1.0 |
| 2. L-(−)-enantiomer of 1 | 1.0 |
| 3. (d,1)-racemate (1 and 2) | 0.8 |
| 4. (d,1)-2-ethoxy-1-[2-trimethylaminoethoxy)phosphinyloxy]hexadecane, hydroxy inner salt | 3.5 |
| 5. (d,1)-2-ethoxy-1-[(2-trimethylaminoethoxy)phosphinyloxy]dodecane hydroxy inner salt | >20 |
| 6. (d,1)-2-ethoxy-1-[(2-trimethoxyaminoethoxy)phosphinyl]octane, hydroxy inner salt | >>20 |
| 7. (d,1)-2-methoxy-1-[(2-trimethylaminoethoxy)phosphinyloxy]eicosane, hydroxy inner salt | 1.5 |
| 8. (d,1)-2-hydroxy-1-[(2-trimethylaminoethoxy)phosphinyloxy]eicosane, hydroxy inner salt | >>20 |

Compounds according to formula II above are also active against transplanted tumors in mice. Table II which follows gives the results of testing (d,1)-2-ethoxy-1-[(2-trimethylaminoethoxy)phosphinyloxy]eicosane, hydroxy inner salt, (A), against several such tumors. In the table, column 1 gives the name of the tumor, column 2 the dosage levels, column 3 toxic deaths, column 4, the percent tumor growth inhibition and column 5, the dosage schedule or regimen. Ten mice were given each dosage I.P. and a group of 20 mice used as controls. The same compound showed no activity against P388 leukemia, M-5 ovarian carcinoma, C$_3$H mammary carcinoma and CA755 mammary carcinoma.

Table III gives the results obtained by comparing the activity of the racemate (d,1)-2-ethoxy-1-[(2-trimethylaminoethoxy)phosphinyloxy]eicosane, hydroxy inner salt (A), the L-(−)enantiomer (B) and the D-(+)enantiomer (C) versus X-5563, a plasma cell myeloma.

TABLE II

Antitumor Activity of (d,1)-2-Ethoxy-1-[(2-trimethylaminoethoxy)-phosphinyloxy]eicosane, hydroxy inner salt (A)

| Tumor | dosage mg/kg | Toxic deaths | Percent inhibition of Tumor growth | Dosage/Regimen |
|---|---|---|---|---|
| C-6 colon | 35 | 5/10 | Toxic | Daily for 10 days |
| carcinoma | 25 | 0/10 | 24 | after tumor inocu- |
|  | 17 | 1/10 | 56* | lation with 5 day |
|  | 12 | 0/10 | 23 | delay |
| 6C3 HED | 35 | 0/10 | 85* | Daily for 8 days |
| lymphosarcoma | 25 | 0/10 | 48* | after inoculation |
|  | 17 | 0/10 | 15 |  |
|  | 12 | 0/10 | 10 |  |
| X-5563 | 70 | 10/10 | toxic | Daily for 10 days |
|  | 50 | 10/10, 10/10 | toxic | with 3 day delay. |
| plasma cell | 35 | 4/10, 5/10 | toxic |  |
| myeloma | 25 | 0/10, 2/10 | 77*, 86* |  |
|  | 17 | 0/10, 0/10 | 65*, 70* |  |
|  | 12 | 0/10 | 37 |  |

TABLE III

Antitumor Activity of Racemate and Enantiomers (A,B,C) Vs X-5563 Plasma Cell Myeloma

| Compound | dosage mg/kg | Toxic deaths | Percent inhibition of Tumor growth | Dosage/Regimen |
|---|---|---|---|---|
| (d,1)-A | 50 | 10/10 | Toxic | daily for 10 day |
|  | 35 | 4/10 | Toxic | with 3 day delay |
|  | 25 | 0/10 | 77 |  |
|  | 17 | 0/10 | 65 |  |
|  | 12 | 0/10 | 37 |  |
| D-(+)-B | 50 | 10/10 | Toxic | Daily for 10 days |
|  | 35 | 5/10 | Toxic | after inoculation |
|  | 25 | 1/10 | 95* |  |
|  | 17 | 2/10 | 76* |  |
| L-(−)-C | 20 | 0/10 | 67* | Daily for 10 days |
|  | 10 | 0/10 | 53* | after inoculation |
|  | 5 | 1/10 | 44 |  |
|  | 2.5 | 1/10 | 18 |  |

Oral dosing of the same drug vs X-5563 plasma cell myeloma orally daily for 10 days after inoculation at 50, 35 and 25 mg/kg gave 56, 47 and 10 percent inhibition of tumor growth, with minimal toxicity 50 and 70 mg/kg dose levels orally were toxic.

The compounds of this invention also inhibit the release of arachidonic acid from membrane phospholipids. In this procedure, glycogen-elicited rabbit neutrophils are labelled with $^{14}C$-arachidonic acid by incubation for one hour at 37° C. and followed by treatment with the compound under test at 37° C. for 5 minutes. The cells were then activated by addition of 0.5 mcg/ml of A-23187 (an ionophore) for 5 minutes. Cellular metabolism was stopped; the membrane lipids extracted; and the extracted lipids chromatographed on TLC plates. Assays were conducted for free $^{14}C$-arachidonic acid and hydroxy$^{14}C$-eicosatetraenoic acid (HETES) using a radiochromatogram scanner. Experimental results showed that (d,1)-2-methoxy-1-[(2-trimethylaminoethoxy)phosphinyloxy]eicosane, hydroxy inner salt, inhibited the release of arachidonic acid (AA) from phospholipids by 88% and inhibited the total production of free AA and HETES by 100%. The corresponding ethoxy compound gave 69% and 97% inhibition respectively.

It is well known that free arachidonic acid may be processed into potent inflammatory mediators such as the leukotrienes, prostaglandins, thromboxane $A_2$ and prostacyclin. Inhibition of the release of arachidonic acid could result in a lowered inflammatory response. Compounds according to II above, which inhibit the release of arachidonic acid, possess anti-inflammatory activity; i.e., (d,1)-2-methoxy-1-[(2-trimethylaminoethoxy)phosphinyloxy]eicosane, hydroxy inner salt inhibited rat paw swelling in the standard carageenin-induced edema (acute inflammation) model by 68% at 4 hours to a group of 5 rats at a 25 mg/kg oral dose level.

The above compounds are also active in lowering the blood pressure of spontaneously hypertensive rats (SHR). For example, racemic (d,1)-2-ethoxy-1-[(2-trimethylaminoethoxy)phosphinyloxy]eicosane, hydroxy inner salt, (A) as well as the L-(−)enantiomer (C), but not D-(+)enantiomer (B), when administered subcutaneously to SHR at various dose levels produced the hypotensive effects set forth in Table IV below. In the table, column 1 gives the compound used, column 2 the dose level, column 3, the route of administration, column 4, number of rats, column 5, the time of blood pressure measurement, column 6, blood pressure in mm (Hg), and column 7, heart rate.

TABLE IV

| Compound | Dose mg/kg | Route of Administration | No. of Rats | Time in Hours | Blood pressure (mm Hg) | Heart Rate |
|---|---|---|---|---|---|---|
| A | 50 | S.C. | 8 | 0 | 190* | 345 |
|  |  |  |  | 1 | 177 | 352 |
|  |  |  |  | 2 | 149 | 355 |
|  |  |  |  | 3 | 143 | 367 |
|  |  |  |  | 4 | 139 | 357 |
|  |  |  |  | 5 | 129 | 359 |
| A | 30 | S.C. | 8 | 0 | 188* | 335 |
|  |  |  |  | 1 | 177 | 328 |
|  |  |  |  | 2 | 151 | 349 |
|  |  |  |  | 3 | 147 | 346 |
|  |  |  |  | 4 | 156 | 347 |
|  |  |  |  | 5 | 151 | 341 |
| A | 5 | S.C. | 5 | 0 | 188* |  |
|  |  |  |  | 1 | 177 |  |
|  |  |  |  | 2 | 159 |  |
|  |  |  |  | 3 | 155 |  |
|  |  |  |  | 4 | 154 |  |
|  |  |  |  | 5 | 156 |  |
| A | 10 | I.V. | 4 | 0 | 198** | 345 |
|  |  |  |  | .08 | 78 | 442 |
|  |  |  |  | .25 | 140 | 420 |
|  |  |  |  | .5 | 153 | 395 |
|  |  |  |  | 1.0 | 154 | 365 |
| A. | 3 | I.V. | 4 | 0 | 195** | 335 |
|  |  |  |  | .08 | 105 | 280 |
|  |  |  |  | .25 | 140 | 337 |
|  |  |  |  | .5 | 153 | 370 |
|  |  |  |  | 1.0 | 173 | 395 |
| Saline control |  |  |  | 0 | 197* | 323 |
|  |  |  |  | 1 | 195 | 307 |
|  |  |  |  | 2 | 187 | 287 |
|  |  |  |  | 3 | 180 | 297 |

TABLE IV-continued

| Compound | Dose mg/kg | Route of Administration | No. of Rats | Time in Hours | Blood pressure (mm Hg) | Heart Rate |
|---|---|---|---|---|---|---|
| | | | | 4 | 178 | 297 |
| | | | | 5 | 173 | 284 |
| B | 3 | I.V. | 3 | 0 | 197** | 326 |
| | | | | .08 | 197 | 373 |
| | | | | .25 | 200 | 400 |
| | | | | .5 | 188 | 346 |
| | | | | 1.0 | 194 | 376 |
| B | 10 | I.V. | 4 | 0 | 183** | 345 |
| | | | | .08 | 185 | 360 |
| | | | | .25 | 184 | 360 |
| | | | | .50 | 177 | 345 |
| | | | | 1.0 | 178 | 355 |
| C | 3 | I.V. | 4 | 0 | 177** | 340 |
| | | | | .08 | 107 | 385 |
| | | | | .25 | 144 | 367 |
| | | | | .5 | 162 | 370 |
| | | | | 1.0 | 162 | 380 |

*B.P. measured by tail cuff method.
**B.P. measured by femoral artery cannula.

The compounds of this invention are usually administered by the parenteral route; i.e., in emulplor ($H_2O$) for ip administration in 5% acacia, in saline for SC administration, in 1.2% ethanol in saline for IV administration. For oral administration, the drug is added to 1% aqueous carboxymethyl cellulose.

We claim:

1. A compound of the structure

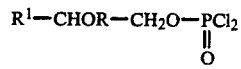

wherein R is $C_{1-6}$ alkyl and $R^1$ is a straight-chain $C_{10-24}$ straight chain alkyl radical.

* * * * *